US006582960B1

(12) United States Patent
Martin et al.

(10) Patent No.: US 6,582,960 B1
(45) Date of Patent: Jun. 24, 2003

(54) USE OF FIBROBLAST GROWTH FACTOR 2 FOR EXPANSION OF CHONDROCYTES AND TISSUE ENGINEERING

(75) Inventors: Ivan Martin, Basel (CH); Lisa E. Freed, Belmont, MA (US); Robert Langer, Newton, MA (US); Gordana Vunjak-Novakovic, Belmont, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/397,417

(22) Filed: Sep. 17, 1999

Related U.S. Application Data

(60) Provisional application No. 60/101,047, filed on Sep. 18, 1998.

(51) Int. Cl.$^7$ .............................. C12N 5/00; C12N 5/08; C12N 15/63; C12N 15/00; C07H 21/04

(52) U.S. Cl. ...................... 435/377; 435/375; 435/405; 435/455; 435/325; 435/395; 435/404; 435/366; 536/23.1

(58) Field of Search ................................ 435/375, 377, 435/455, 325, 404, 405, 440, 366, 372, 395; 536/23.1

(56) References Cited

U.S. PATENT DOCUMENTS

| | | | |
|---|---|---|---|
| 5,512,600 A | | 4/1996 | Mikos et al. |
| 5,667,778 A | | 9/1997 | Atala |
| 5,716,404 A | | 2/1998 | Vacanti et al. |
| 5,861,315 A | * | 1/1999 | Nakahata ..................... 435/384 |
| 5,919,702 A | * | 7/1999 | Purchio et al. ............. 435/378 |
| 6,150,163 A | * | 11/2000 | McPherson et al. ........ 435/384 |

FOREIGN PATENT DOCUMENTS

| | | |
|---|---|---|
| WO | WO 94/16718 | 8/1994 |
| WO | WO 96/18424 | 6/1996 |
| WO | WO 98/04681 | 2/1998 |
| WO | WO 98/17791 | 4/1998 |
| WO | WO 98/32333 | 7/1998 |

OTHER PUBLICATIONS

Kondo, et al. Oligodendrocyte Precursor Cells Reprogrammed to Become Multipotential CNS Cells, Science, vol. 289, pp. 1754–1757, Sep. 8, 2001.*
Martin, et al. Endocrinology vol. 138, No. 10, pp. 4456–4462, Oct. 1997.*
Toolan, et al. Journal of Biomedical Materials Research vol. 31, pp. 273–280, 1996.*
Inoue, et al., "Stimulation of Cartilage–Matrix Proteoglycan Systhesis by Morphologically Transformed Chondrocytes Grown in the Presence of Fibroblast Growth Factor and Transforming Growth Factor–Beta" *Journal of Cellular Physiology*, 138(2): 329–337, 1989.

Quarto, et al., "Proliferation and Differentiation of Chondrocytes in Defined Culture Medium: Effects of Systemic Factors", *Bone*: 17(6) 588, 1995.
Quarto, et al., "Modulation of Commitment, Proliferation, and Differentiation of Chondrogenic Cells in Defined Culture Medium", *Endocrinology*, 138: 4966–4976, 1997.
Yaeger, et al., "Synergistic Action of Transforming Growth Factor–β and Insulin–Like Growth Factor–1 Induces Expression of Type II Collagen and Aggrecan Genes in Adult Human Articular Chondrocytes", *Experimental Cell Research*:237: 318–325, 1997.
Freed et al., "Joint Resurfacing Using Allograft Chondrocytes and Synthetic Biodegradable Polymer Scaffolds" *Biomed. Mat. Res.*, 28:891–899, 1994.
Kato et al., "Sulfated Proteoglycan Synthesis by Confluent Cultures of Rabbit Costal Chondrocytes Grown in the Presence of Fibroblast Growth Factor" *J. Cell Biol.*, 100(2):477–485, Feb. 1985.
Kato et al., "Fibroblast Growth Factor is an Inhibitor of Chondrocyte Terminal Differentiation" *J. Biol. Chem.*, 265(10):5903–5909, 1990.
Langer et al., "Tissue Engineering" *Science*, 260:920–926, May 14, 1993.
Langer et al., "Future Directions in Biomaterials" *Biomaterials*, 11:738–745, 1990.
Minas et al., "Current Concepts in the Treatment of Articular Cartilage Defects" *Orthopedics*, 20(6): 525–538, Jun. 1997.
Rheinwald et al., "Serial Cultivation of Strains of Human Epidermal Keratinocytes: the Formation of Keratinizing Colonies from Single Cells" *Cell*, 6:331–344, Nov. 1975.
Toolan et al., "Effects of Growth–Factor–Enhanced Culture on a Chondrocyte–Collagen Implant for Cartilage Repair" *Biomed Mater Res.*, 31(2):273–280, Jun. 1996.
Vacanti et al., "Selective Cell Transplantation Using Bioabsorbable Artificial Polymers as Matrices" *J. Pediatr. Surg.*, 23(1):3–9, Jan. 1988.
Vacanti et al., "Beyond Transplantation" *Arch. Surg.*, 123:545–549, May 1988.

(List continued on next page.)

*Primary Examiner*—David Guzo
*Assistant Examiner*—Gerald G. Leffers, Jr.
(74) *Attorney, Agent, or Firm*—Banner & Witcoff, Ltd.

(57) ABSTRACT

The present invention provides an improved method for expanding cells for use in tissue engineering. In particular the method provides specific biochemical factors to supplement cell culture medium during the expansion process in order to reproduce events occurring during embryonic development with the goal of regenerating tissue equivalents that resemble natural tissues both structurally and functionally. These specific biochemical factors improve proliferation of the cells and are capable of de-differentiation mature cells isolated from tissue so that the differentiation potential of the cells is preserved. The bioactive molecules also maintain the responsiveness of the cells to other bioactive molecules. Specifically, the invention provides methods for expanding chondrocytes in the presence of fibroblast growth factor 2 for use in regeneration of cartilage tissue.

21 Claims, 4 Drawing Sheets

OTHER PUBLICATIONS

Wakitani et al., "Mesenchymal Cell–Based Repair of Large, Full–Thickness Defects of Articular Cartilage" *J. Bone Joint Surg*, 76–A(4):579–592, Apr. 1994.

Wroblewski et al., "Inhibitory Effects of Basic Fibroblast Growth Factor on Chondrocyte Differentiation" *J. Bone Miner. Res.*, 10(5):735–742, May 1995.

Benya et al., "Dedifferentiated Chondrocytes Reexpress the Differentiated Collagen Phenotype When Cultured in Agarose Gels" *Cell* 30:215–224, Aug. 1982.

Brittberg et al., "Treatment of Deep Cartilage Defects in the Knee with Autologous Chondrocyte Transplantation" *N. Engl J. Med.*, 331:889–895, Oct. 6, 1994.

Brittberg et al., "Rabbit Articular Cartilage Defects Treated with Autologous Cultured Chondrocytes" *Clin. Orthop.*, 326:270–283, May 1996.

Butnariu–Ephrat et al., "Resurfacing of Goat Articular Cartilage of Chondrocytes Derived From Bone Marrow" *Clin. Orthop.*, 330:234–243, 1996.

Cima et al., "Hepatocyte Culture on Biodegradable Polymeric Substrates" *Biotechn.Bioeng.*, 38:145–158, 1991.

* cited by examiner

I　　　　　　II　　　　　　III

USE OF FIBROBLAST GROWTH FACTOR 2 FOR EXPANSION OF CHONDROCYTES AND TISSUE ENGINEERING

This application claims priority under 35 U.S.C. 119(e) to the provisional U.S. application Ser. No. 60/101,047 entitled "Use of Growth Factors and Hormones for Expansion of Mammalian Cells and Tissue Engineering," by Martin et al., filed Sep. 18, 1998 and hereby incorporated in its entirety by reference.

This invention was made with U.S. government support under Grant Number NAG9-836 awarded by the NASA. The U.S. Government has certain rights in the invention.

BACKGROUND OF THE INVENTION

Nearly 8 million surgical procedures are performed annually in the United States alone to treat tissue and organ dysfunction. Tissue engineering is the development of biological substitutes to restore, maintain, or improve tissue function. Specifically, tissue engineering is a method by which new living tissue are created in the laboratory to replace diseased or traumatized tissue (Langer et al., *Science*, 260:920–926, 1993).

One particular strategy that has been created to regenerate new tissue is to (i) isolate specific cells from tissue; (ii) expand the isolated cells in vitro; and (iii) implant the expanded cells into the diseased or traumatized tissue so that the implanted cells proliferate in vivo and eventually replace or repair the tissue defect (Langer et al., supra). This technique has been applied to a variety of cell types and tissue defects (for example see Brittberg et al., *N. Engl. J. Med.*, 331:889–895, 1994; Rheinwald et al., *Cell*, 6:331–344, 1975; Langer et al., supra). Isolated cells could be either differentiated cells from specific tissues or undifferentiated progenitor cells (stem cells). In both cases, establishment of appropriate culture conditions for cell expansion is extremely important in order to maintain or improve their potential to regenerate structural and functional tissue equivalents (Rheinwald et al., supra)

A particular area of focus for the development of tissue regeneration techniques has been correction of defects in cartilagenous tissue. Unlike other tissues, cartilage has little ability to regenerate itself after trauma, disease or as a result of old age. This is due to the avascular nature of normal articular cartilage. Although damage to the superficial chondral plate generally does not heal, the subchondral bone is vascularized, therefore damage to this location does heal to a limited degree. The new cartilage that grows in place of the damaged articular cartilage is called fibrocartilage. Fibrocartilage lacks the durability and more desirable mechanical properties of the original hyaline cartilage. People who suffer joint damage are thereafter predisposed to arthritic degeneration (Freed et al., *J. Biomed. Mat. Res.*, 28:891–99, 1994; Minas et al., *Orthopedics*, Jun. 20(6):525–538, 1997).

Several different approaches have been taken to repair cartilage tissue. In a method utilizing cartilage explants, cartilage is removed from a body and cultured in vitro for implantation into articular cartilage defects (Sah et al., *J. Orthop. Res.*, Jan. 14 (1):44–52, 1996). Other more current approaches for articular cartilage repair typically consist of harvesting chondrocytes from cartilagenous tissue and seeding the chondrocytes directly onto a three dimensional transplantation matrix material before implantation of the replacement tissue into the damaged area (Freed et al., supra). This technique results in high quality cartilage once regeneration is complete, however this technique requires a large quantity of starting material to be harvested from the patient, resulting in increased patient trauma.

Chondrocytes are isolated from a biopsy, expanded in monolayer cultures until a sufficient number of cells are obtained and implanted into the damaged area of tissue. Implantation requires first, that the cells are either embedded in a gel or associated with a biodegradable polymer scaffold (Brittberg et al., *Clin. Orthop.*, May 326:270–283, 1996; Minas et al., supra; Freed et al., supra; ). The three dimensional nature of these matrices imparts structural integrity to the implant and provides rigid support for growth of the chondrocyte cells into cartilagenous tissue. Although this system has the advantage of requiring fewer cells as starting material, the cartilage obtained by this methods is often of poor quality if the cells are harvested or obtained from skeletally mature donors (adults). Alternatively, progenitor cells from the bone marrow are expanded and used to repair full-thickness defects involving both the articular surface and the underlying subchondral bone (Wakitani et al., *J. Bone Joint Surg*, 76-A:579–592,1994: Butnariu-Ephrat et al., *Clin. Orthop*, 330:234–243, 1996).

A distinct challenge presented by this system has been to increase the proliferation rate of the cells during the expansion phase in a manner that results in successful regeneration.

There exists a need for improved expansion techniques for cells that are to be used in tissue engineering.

SUMMARY OF THE INVENTION

The present invention pertains to an improved method of expanding cells for use in tissue engineering. It is an aspect of the present invention that expanding cells in the presence of growth factors and hormones stimulates proliferation of the cell population while preserving the properties of the cells necessary for regenerating high quality tissue. It is another aspect of the present invention to provide methods for regenerating tissues with better structural and functional characteristics by recapitulating events occurring during embryonic development. It is yet another aspect of the present invention to provide methods of maintaining or improving the ability of the expanded cells to respond to differentiation stimuli as they regenerate new tissue in vitro or in vivo.

The method of the present invention includes: (i) providing a cell population; (ii) expanding the cell population in the presence of specific biochemical factors; and (iii) using the cells for tissue engineering. A variety of cell types can be used in the present invention. According to the present invention, any cell type desirable for use in tissue engineering that can be isolated is used to regenerate tissue. Non-limiting examples include endothelial cells, muscle cells, chondrocytes and melanocytes. Additionally, any of a variety of biochemical factors that increase proliferation of the cells without losing the quality of the cell can be used in the process of cell expansion. Non-limiting examples of biochemical factors that may be used in the present invention are chondromodulins, platelet derived growth factors, epidermal growth factors, fibroblast growth factor 2, transforming growth factor beta, insulin like growth factors, bone morphogenetic proteins, epidermal growth factor, and platelet derived growth factors.

In a preferred embodiment of the present invention, cartilage tissue for tissue engineering is regenerated using the teachings of the present invention. The present invention demonstrates that chondrocytes isolated from mature cartilage tissue can be expanded in the presence of fibroblast growth factor-2 (FGF-2) and then used to regenerate cartilage tissue. Specifically, FGF-2 added to culture medium during cell expansion helps the cells maintain their potential to regenerate cartilaginous tissue. Specifically, FGF-2 decreases the doubling time of the cell population, while creating a cell population with a homogeneous de-differentiated state and preserving their ability to respond to environmental changes such as responses to growth factors like insulin.

In another preferred embodiment, chondrocytes, preferably mammalian, and more preferably human, are isolated from mature cartilage tissue and expanded in vitro in the presence of fibroblast growth factor 2 (FGF-2) and transforming growth factor beta1 (TGFβ). This expansion allows the de-differentiation of cells while maintaining their full potential for redifferentiation in response to environmental changes.

In another preferred embodiment, the expansion and dedifferentiation of human chondrocytes results in cells that can be redifferentiated into primary chondrocytes for use in tissue engineering. Redifferentiation is performed preferably in a serum-free medium. More preferably, redifferentiation is performed in a serum-free medium containing insulin, transforming growth factor beta (TGFβ), and dexamethasone. Most preferably, redifferentiation is performed in a serum-free medium containing insulin, transferrin, selenous acid, linoleic acid, albumin, ascorbic acid, transforming growth factor beta (TGFβ), and dexamethasone.

In another preferred embodiment, expansion of cells in the presence of biochemical growth factors for use in tissue engineering also improves the efficiency of tranfection of nucleic acids into the cells. Typically, gene transfer is carried out during monolayer expansion. Therefore, applications where tissue engineering techniques are combined with gene therapy may be utilized in accordance with the teachings of the present invention.

DEFINITIONS

"De-differentiation": "De-differentiation" is used herein to describe cells that lack differentiated functions and to imply regression to an earlier bipotent or multipotent embryonic state. For example, when chondrocytes from cartilage tissue are released from the cartilage matrix and placed in a monolayer culture, they stop producing characteristic markers that define them as being differentiated. Two such markers for differentiated chondrocyte cells are two well characterized structural macromolecules, cartilage proteoglycan and type II collagen.

"Bioactive molecule" or "biochemical factor": "Bioactive molecule" or "biochemical factor" is used herein to refer to any chemical or protein that can elicit any metabolic response from a cell. A biochemical factor can be a protein, for example a hormone or a growth factor that will stimulate a specific biochemical pathway in the cell. A biochemical factor can also be a simple chemical such as a chemotherapeutic agent. "Bioactive molecule" is also encompassing of any hydrodynamic factor or signal.

"Expand": "Expanding", "expanded", or expand is used herein to refer to the process or growing cells in vitro.

DETAILED DESCRIPTION OF THE INVENTION

Cells to Be Implanted

Figure 1A:
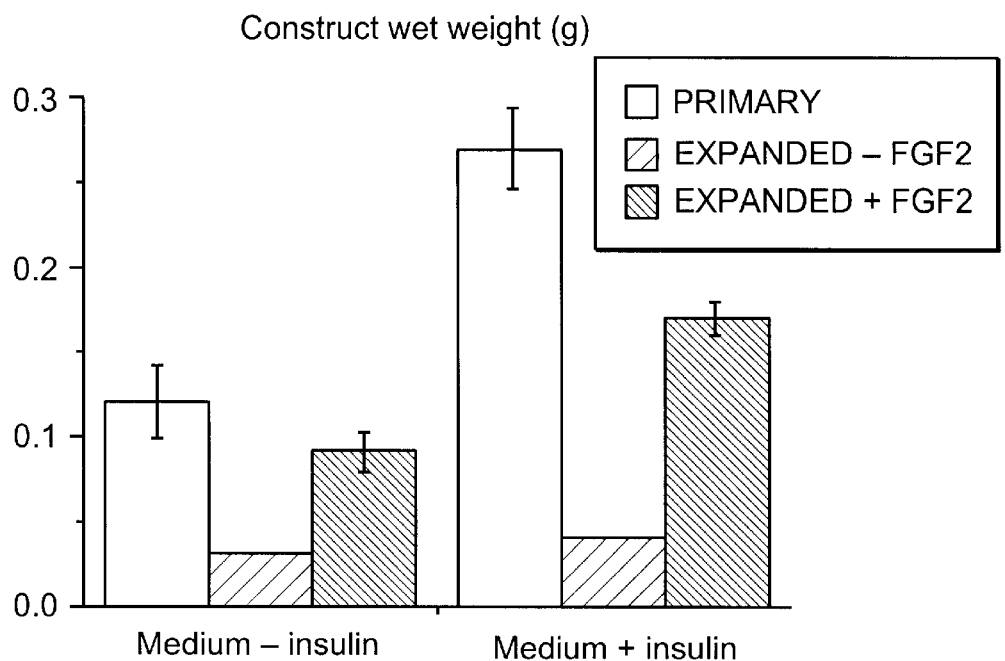
FIG. 1A is a graph representing the weight of the engineered construct grown from either primary chondrocytes or chondrocytes expanded with or without FGF-2 in the presence or absence of insulin.

The present invention provides improved methods of tissue engineering. In particular, the invention provides improved approaches to expanding cells for use in tissue engineering applications. The basic theory underlying the present invention is that in order to regenerate tissues with better structural and functional characteristics, it is desirable to recapitulate events occurring during embryonic development. In one preferred embodiment, cells isolated from a mature tissue are expanded and de-differentiated in the presence of specific biochemical factors in order to preserve their differentiation potential. In this way, the cells may be better able to respond to differentiation stimuli when they regenerate new tissue in vitro or in vivo.

Specifically, the present invention provides methods for improved expansion of various cell types that can be used in tissue engineering. In one preferred embodiment, the present invention provides growth factors to the cell culture medium to promote proliferation of the cells while maintaining the differentiation potential of the cells. To give but a few examples, growth factors that can be used in the present invention include chondromodulins, platelet derived growth factors, epidermal growth factors, heparin binding factor, transforming growth factor alpha and beta, alpha fibroblastic growth factor, fibroblast growth factor 2, insulin like growth factors, bone morphogenetic proteins, and vascular endothelium growth factor. In another embodiment, the invention provides hormones (e.g., insulin glucagon or estrogen) to the cell culture medium to promote proliferation of the cells while maintaining the differentiation potential of the cells. In still other preferred embodiments, angiogenic factors may be used for in vitro expansion.

Those of ordinary skill in the art will appreciate the variety of cell types to which this method of cell expansion can be applied. Tissue engineering techniques have been used to correct defects in a myriad of different cell types. Tissue engineering can be applied to the correction of hard tissue defects, such as defects in cartilage or bone that arise from disease or trauma. Tissue engineering has also been applied to the correction of soft tissue structures. By way of example, cells used in the current invention can be used to regenerate metabolic organs (e.g., the liver or pancreas), epidermal tissue (e.g., of burn victims) or to reconstruct or augment breast tissue (e.g., muscle cells may be used to reconstruct the breast of women afflicted with breast cancer, congenital defects, or damage resulting from trauma; see U.S. Pat. No. 5,512,600 and WO/96/18424, both of which are incorporated herein by reference). Furthermore, congenital defects such as vesicoureteral reflux, or incontinence can be corrected by implantation of a gel or scaffolding matrix seeded with muscle cells in an effective amount to yield a muscle area that provides the required control over the passage of urine or otherwise corrects the defect (U.S. Pat. No. 5,667,778; incorporated herein by reference).

According to the present invention, the cells used to reconstruct or augment the specific physical location can be different from the cells that normally constitute that tissue in the body. For example, chondrocytes can be used to correct soft tissue defects by serving as a bulking agent (U.S. patent application, Ser. No. 08/654,844, Now U.S. Pat. No. 6,060,053). In certain preferred embodiments, multiple cell types are used to create a single regenerated tissue. In each case, it is important that the cells of the present invention are expanded and de-differentiated in the presence of specific biochemical factors, without losing the cellular properties required for successful tissue regeneration.

Many different biochemical factors can be used in the present invention. Specific biochemical factors are preferably able to stimulate proliferation of the relevant cells in vitro and are able to promote de-differentiation of differentiated cells isolated from mature tissue. According to the present invention, a factor that, when added to tissue culture medium during expansion of the isolated cells, decreases the doubling time of that cell population is preferred. The present invention also provides factors that, when added to tissue culture medium have the effect of reversing the differentiation process of a particular mature cell type, or maintaining the differentiation potential of an immature cell type. Particularly preferred are biochemical factors that both decrease the doubling time of the particular cell population and preserve the differentiation potential. Such characteristics reproduce an embryonic environment for the cell and promote regeneration of quality tissue for such applications as described above. Without wishing to limit the invention, some examples of biochemical factors that can be used in the present invention are chondromodulins, platelet derived growth factors, epidermal growth factor, fibroblast growth factor 2, transforming growth factor beta, insulin like growth factors, and bone morphogenetic proteins.

The condition of the expanded cells significantly affects the successful regeneration of quality tissue. Therefore, the growth environment of the cells during in vitro expansion of cells preferably promotes optimization of the expansion process. In the present invention, it is preferable that the expanded cells are homogeneous with respect to their stage of differentiation. According to the present invention, the growth environment may be manipulated by the addition of growth factors and/or hormones to achieve a homogeneous population of de-differentiated cells.

In a particularly preferred embodiment, chondrocytes are expanded by the methods of the present invention for the regeneration of cartilage tissue. Specifically, chondrocytes isolated from a subject are expanded in the presence of growth factors that increase the proliferation rate of the chondrocytes while preserving the appropriate differentiation properties of the cells to ensure successful regeneration of high quality cartilage tissue for implantation.

Prior to the present invention, cartilage tissue was maintained in tissue culture one of two ways: (i) cartilage tissue was isolated from the body and propagated in in vitro tissue culture (tissue explant), or (ii) primary chondrocyte cells isolated from cartilage tissue were seeded onto a three dimensional polymeric scaffold and allowed to proliferate and differentiate on the scaffold to form cartilage tissue (tissue implants). Efforts to first expand the chondrocyte cells in in vitro monolayer cultures, prior to seeding the three dimensional polymeric scaffold were generally unsuccessful in that the cartilage tissue obtained from such efforts was of poor quality compared to the cartilage tissue obtained by seeding the polymeric scaffold with freshly isolated primary chondrocytes.

It is known that mammalian cells (e.g., chondrocytes and bone) in a three dimensional environment respond very differently to stimuli (e.g., biochemical factors and hydrodymanic factors or signals) than do cells in monolayer cultures. It has been demonstrated that the differentiated phenotype of chondrocyte cells can be stabilized by transferring them from a monolayer culture into a three dimensional environment (Benya et al., *Cell*, 30:215–224, 1982; incorporated herein by reference). Chondrocyte cells in monolayer culture typically form differentiated fibroblast cells (Kato et al., *J. Cell Biol.*, February, 100(2):477–485, 1985). This loss of the chondrocytic phenotype in monolayer culture contributes to the inability of expanded cells to successfully seed and regenerate cartilage tissue that is equivalent to cartilage tissue formed by freshly isolated primary chondrocytes directly seeded onto the polymeric matrix. A particular challenge is to increase the cell mass without losing the quality of the cell and thus also the resulting regenerated cartilage tissue.

Fibroblast growth factor (FGF-2) has been applied in vitro to chondrocyte cells both in monolayer culture and in three dimensional environments. It has been established that fibroblast growth factor 2 (FGF-2) (also called basic fibroblast growth factor) is a potent mitogen for chondrocytes in monolayer culture and in vivo (Wroblewski et al., *J. Bone Miner. Res.*, May, 10(5):735–742, 1995; Kato et al., *J. Biol. Chem.*, 265:5903–5909, 1990), However, reports about the use of FGF-2 to culture cartilage tissue in vitro in a three dimensional environment have been contradictory. For example, FGF-2 has been reported both (i) cause a waning of the mature phenotypic characteristics typical of cartilage explants (Sah et al., supra), and (ii) increase the rate of proliferation without affecting the mature phenotypic characteristics of chondrocyte-seeded implants in the presence of FGF-2 (Toolan et al., *J. Biomed Mater Res.*, June 31(2): 273–280, 1996).

Although chondrocytes have been cultured in the presence of FGF-2, and FGF-2 has been used to culture chondrocyte seeded implants, FGF-2 expanded chondrocytes have not previously been used for tissue engineering or regeneration. Given the varied effects FGF-2 has on chondrocytes in monolayer cultures versus on polymeric scaffold, there was no reasonable expectation that using cells expanded in FGF-2 to seed three dimensional matrices would be successful.

The present invention pertains to the use of FGF-2 as a culture medium supplement in order to optimize in vitro expansion of mammalian chondrocytes. The present invention demonstrates that when FGF-2 is added to the culture medium during the expansion phase, not only do chondrocytes proliferate faster, but they also retain a higher potential to regenerate cartilaginous tissue equivalents (see Example 1). Faster proliferation also decreases the initial amount of tissue needed and/or the time required to obtain a sufficient amount of cells to seed onto a scaffold or gel structure. Without wishing to be bound by any particular theory, we propose that FGF-2 is effective not in inducing chondrogenic differentiation of regenerating tissue, but in preserving the chondrogenic differentiation potential of chondrocytes during their in vitro expansion of chondrocyte cells. These results suggest that expansion of chondrocytes in medium containing FGF-2 helps preserve their potential to regenerate cartilaginous tissue. Therefore, chondrocytes expanded with FGF-2 represent a cell population with a higher potential for repairing cartilage defects than chondrocytes expanded in culture medium lacking FGF-2. It is particularly preferred that chondrocytes are expanded in the presence of FGF-2 prior to seeding an implantation matrix at which time further proliferation on the matrix can be performed in the presence or absence of FGF-2.

In another preferred embodiment of the present invention, mammalian chondrocytes, preferably human, are expanded in a medium containing fibroblast growth factor-2 (FGF-2) and preferably also containing transforming growth factor beta (TGFβ). As previously discussed, expansion of chondrocytes in cell culture medium allows the de-differentiation of cells while maintaining their full potential for redifferentiation in response to environmental changes and produces cells that are useful for regenerating cartilage through tissue engineering.

Furthermore, human chondrocytes expanded in a cell culture medium containing FGF-2 and TGFβ are preferentially redifferentiated into primary chondrocytes in a cell culture medium substantially free of serum. Preferably, the serum-free cell culture medium also contains insulin, TGFβ and dexamethasone. Even more preferably, the serum-free cell culture medium contains insulin, transferrin, selenous acid, linoleic acid, albumin, ascorbic acid, transforming growth factor beta (TGFβ), and dexamethasone. Experiments described in Example 2 demonstrate that human chondrocytes that are expanded in cell culture medium in monolayers to induce the highest proliferation rate, subsequently produce the highest levels of redifferentiation markers if expanded in the presence of TGFβ and FGF-2. Furthermore, redifferentiation of expanded human chondrocytes produces the highest levels of differentiation markers if cultured in a serum-free cell culture medium containing insulin, TGFβ and dexamethasone.

In another aspect of the present invention, it is desirable that cells prepared for seeding implantation matrices be responsive to other biochemical factors and signals. Chondrocytes freshly isolated from cartilagenous tissue are normally responsive to insulin which causes increased proliferation of the chondrocytes. The present invention demonstrates that chondrocytes first expanded in the presence of FGF-2 are responsive to insulin in a manner similar to chondrocytes harvested directly from cartilage tissue and seeded directly onto the implantation matrix without an intervening expansion step (see Example 1). Since FGF-2 expanded chondrocytes are highly responsive to insulin in a similar fashion as freshly harvested chondrocytes, they might represent an appropriate cell population for cartilage regeneration in those therapies involving the use of additional hormones and growth factors to further stimulate tissue regeneration.

Generally, it is preferred that any cell type used in the practice of the present invention be able to receive and respond to environmental stimuli present in vitro or in vivo during the process of tissue regeneration. Preferably the cells are heterologous cells. Alternatively, the cells are isolated from a close relative or from an individual of the same species. It will be appreciated by those of ordinary skill in the art that a cell population that is responsive to proliferation or differentiation cell stimuli will be advantageous for use in tissue engineering. A cell population that can respond better to such stimuli will regenerate more quickly, more dependably and as a result yield a higher quality tissue for implantation. In certain embodiments of the present invention, it is desirable to add bioactive molecules to the cells during the regeneration process. A variety of bioactive molecules can be delivered using, for example, matrices described in U.S. Pat. No. 5,716,404 (see below). In one particularly preferred embodiment of the present invention, FGF-2 is used to improve expansion of various cell types (e.g., endothelial cells, muscle cells, melanocytes, hepatocytes, mesenchymal stem cells).

In another preferred embodiment, proteins other than FGF-2 (e.g., chondromodulins) are used to further improve chondrocyte expansion. Any bioactive molecule that improves the proliferation, differentiation potential or quality of the resulting regenerated tissue can be used according to the present invention.

In yet another preferred embodiment, expansion of cells in the presence of biochemical growth factors for use in tissue engineering also improves the efficiency of tranfection of nucleic acids into the cells. Typically, gene transfer is carried out during monolayer expansion. Therefore, applications where tissue engineering techniques are combined with gene therapy may be utilized in accordance with the teachings of the present invention. For example without limitation, cells may be transfected with a vector which confers resistance to a variety of biological and chemical compounds. These compounds include but are not limited to antibiotics, cytokines and inflammatory agents.

Implantation

Dissociated cells are implanted in combination with suitable biodegradable, polymeric matrix to form new tissue. There are two forms of matrices which can be used: a polymeric hydrogel formed of a material such as alginate having cells suspended therein, and a fibrous matrix having an interstitial spacing between about 100 and 300 microns. Preferred polymeric matrices are those degrading over about one to two months, such as polylactic acid-glycolic acid copolymers. The matrices can be seeded prior to implantation or implanted, allowed to vascularize, then seeded with cells. For a detailed description of hydrogel polymer solutions and polymeric matrices, and other methods of implantation see U.S. Pat. No. 5,716,404, incorporated herein by reference. For other methods of using biodegradable polymers to regenerate metabolic organs and other tissues, for example cartilage see Cima et al., Biotechn. Bioeng., 38:145–158, 1991; Langer et al., *Biomaterials,* 11:738–745, 1990; Vacanti et al., *J. Pediatr. Surg.*, 23:3–9, 1988; and Vacanti et al., *Arch. Surg.*, 123:545–549, 1988, all of which are incorporated herein by reference.

In some embodiments, the cell-matrix structures are implanted in combination with tissue expander devices. As the cell-matrix is implanted, or cells proliferate and form new tissue, the expander size is decreased, until it can be removed and the desired reconstruction or augmentation is obtained.

As previously mentioned, other materials, such as bioactive molecules that enhance vascularization of the implanted tissue and/or inhibit ingrowth of fibrotic tissue, can be implanted with the matrix to enhance development of more normal tissue.

The present invention will now be illustrated by the following Examples, which are not meant to limit the scope of the invention. Other aspects, advantages, and modifications within the scope of the invention will be apparent to those skilled in the art to which the invention pertains. The following examples are intended to provide those of ordinary skill in the art with a complete disclosure and description of how to make and use the novel methods of the invention, and are not intended to limit the scope of what the inventors regard as their invention in any way.

EXAMPLES

Example 1
Use of FGF-2 in the Optimization of in vitro Expansion of Mammalian Chondrocytes Results demonstrate that if FGF-2 is added to the culture medium during the expansion phase, not only do chondrocytes proliferate faster, which decreases the initial amount of tissue needed and/or the time required, but also they retain a higher potential to regenerate cartilaginous tissue equivalents.

Bovine articular chondrocytes were expanded in monolayers. By the addition of 5 ng/ml FGF-2 to the culture medium, the proliferation rate was significantly increased (doubling times were 13.9±0.6 and 18.9±1.0 hours for cells expanded with and without FGF-2, respectively). Bovine chondrocytes, expanded by approximately 10 doubling with and without FGF-2 (5 ng/ml), as well as freshly harvested primary chondrocytes, were seeded onto biodegradable polymer scaffolds (nonwoven meshes made of a poly (glycolic acid), PGA) as previously described (Freed et al., supra). The resulting cell-polymer constructs were cultured in medium containing 10% fetal bovine serum, without (control) or with the addition of 5 ng/ml insulin. FGF-2 was not supplemented to the culture medium in any group at this stage. After 6 weeks in culture, constructs were blotted dry, weighed and assessed biochemically for the content of glycosaminoglycans (GAG; FIG. 1), one of the main component of cartilage extracellular matrix. Duplicate samples were processed histologically and stained for collagen type II (FIGS. 2 and 4).

FGF-2 expanded chondrocytes were able to regenerate cartilaginous constructs that were significantly larger in size than those based on chondrocytes expanded in control medium and approached the size of constructs based on freshly harvested chondrocytes (FIG. 1A). The addition of insulin to the culture medium induced a significant increase in the final weight of the constructs based on freshly harvester chondrocytes and on FGF-2 expanded chondrocytes, while chondrocytes expanded in control medium were not significantly responsive to insulin.

Figure 1B:
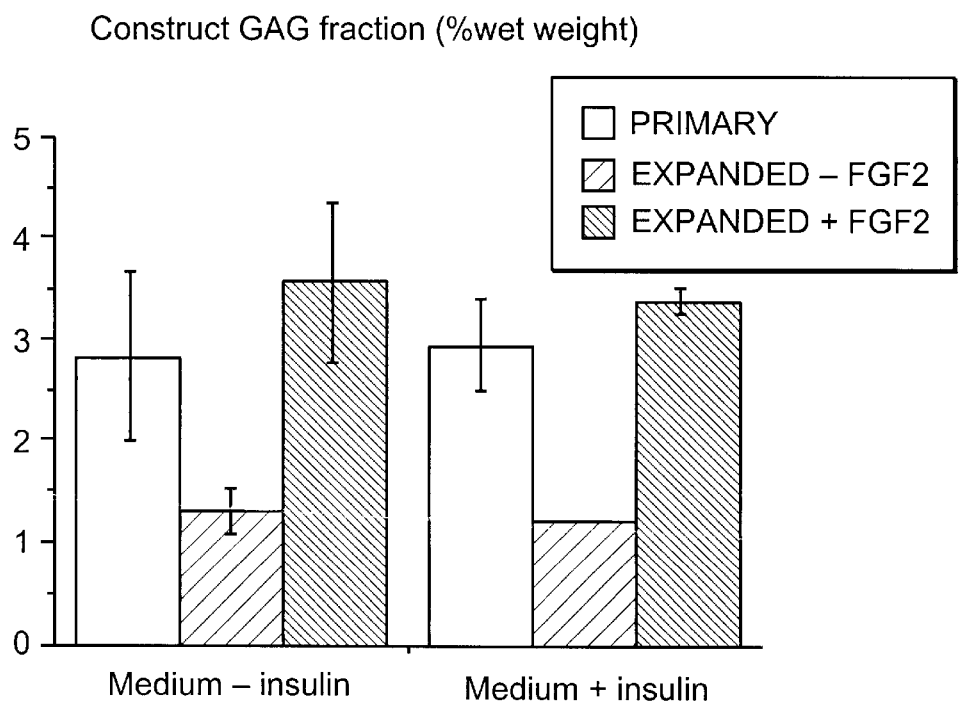
FIG. 1B is a graph representing the percent wet weight of glycosaminoglycan of constructs grown from either primary chondrocytes expanded with or without FGF-2 in the presence or absence of insulin.

The GAG fraction (percentage of construct wet weight) in constructs based on freshly harvested chondrocytes was comparable to that in constructs based on FGF-2 expanded chondrocytes, and significantly higher than that in constructs based on chondrocytes expanded in control medium. The same trend was observed when insulin was added to the culture medium (FIG. 1B). Collagen type II was abundant in constructs based on primary and FGF-2 expanded chondrocytes, and not detectable if cells where expanded without FGF-2.

Figure 2:
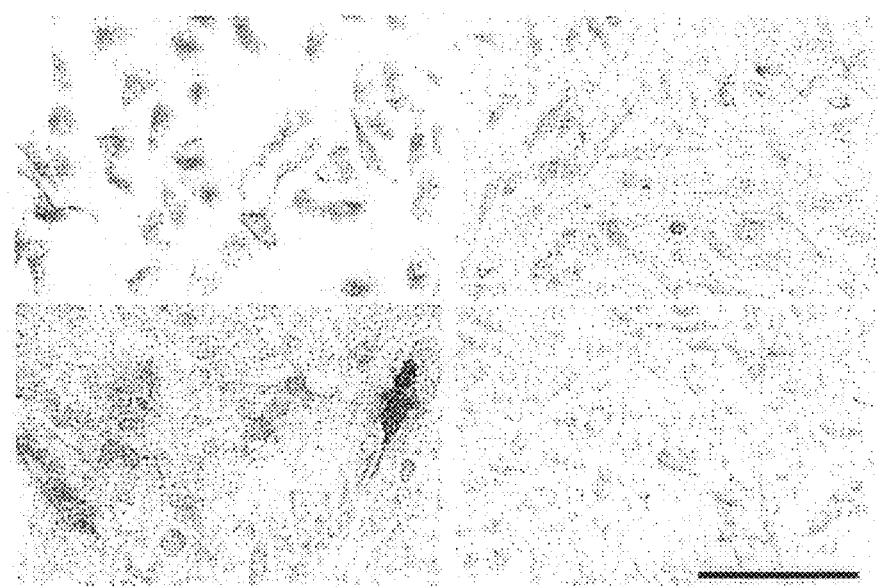
FIG. 2. Collagen type II stain of chondrocyte monolayers. Chondrocytes expanded without (A, C) or with (B, D) FGF-2 after the first (A, B) and second (C, D) passage. FGF-2-expanded chondrocytes displayed lower levels of type II collagen, suggesting faster and more homogeneous dedifferentiation. Scale bar=100 μm.

The presence of FGF-2 during chondrocyte expansion increased the proliferation rate during the first passage (Table 1) and accelerated the process of dedifferentiation, as assessed by the reduced expression of AP (Table 1) and collagen type II (FIG. 2). AP activity decreased with serial passage and at a rate that was higher in the presence of FGF-2 (Table 1). Collagen type II was generally detected in P1 chondrocytes, but the fraction of cells that were positive and the intensity of the stain were both higher for cells expanded without FGF-2 (FIGS. 2A and 2B). Collagen type II was expressed by only a few P2 cells expanded without FGF-2 (FIG. 2C), and was not detected in any P2 cells expanded with FGF-2 (FIG. 2D). Collagen type I was expressed at similar levels in cells expanded with or without FGF-2 (data not shown).

Figure 3A:
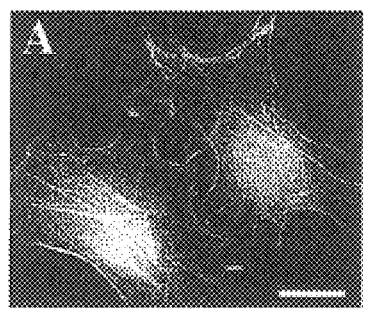
FIG. 3 (Panels A–D). F-actin stain of chondrocyte monolayers. Chondrocytes expanded for two passages in medium without FGF-2 (A), with (B) FGF-2, and in medium with FGF-2 only during the first passage (C) or only during the second passage (D). Chondrocytes expanded without FGF-2 displayed thick F-actin fibers. Scale bar=10 μm.
Figure 3B:
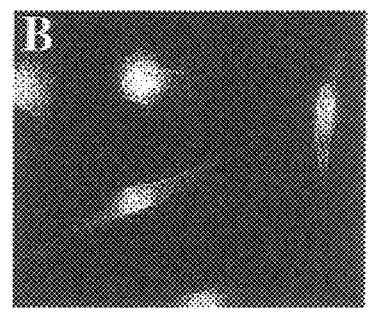
Figure 3C:
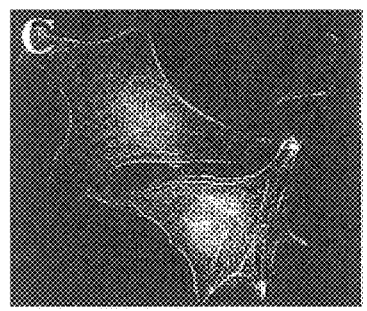
Figure 3D:
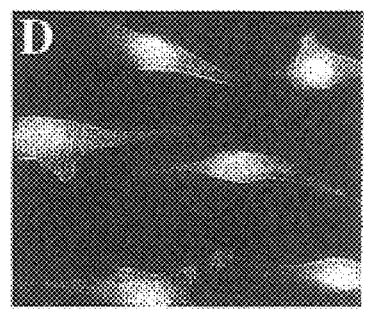
Figure 4A:
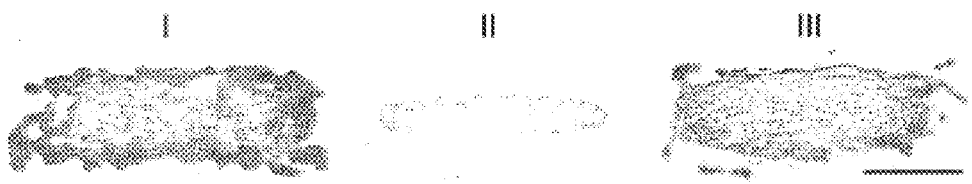
FIG. 4 (Panels A–F). Glycosaminoglycan (GAG) and collagen type II stain of chondrocyte-polymer constructs. Constructs based on primary chondrocytes (I), and chondrocytes expanded for two passages without FGF-2 (II) and with FGF-2 (III), after 1 week (A,B,C) and 6 weeks (D,E,F) of cultivation. Histological sections were stained with Safranin O for GAG (A,B,D,E) or with a monoclonal antibody to type II collagen (C,F). Primary and FGF-2-expanded chondrocytes deposited a continuous ECM containing high concentrations of GAG and type II collagen, while chondrocytes expanded without FGF-2 induced contraction of the polymer scaffold and resulted in constructs with low amounts of GAG and non detectable amounts of type II collagen. Arrows indicate polymer fibers. Scale bar=2 mm (A,D) or 100 μm (B,C,E,F).
Figure 4B:
Figure 4C:
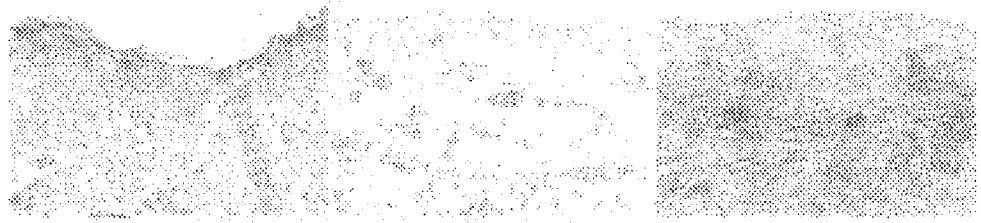
Figure 4D:
Figure 4E:
Figure 4F:
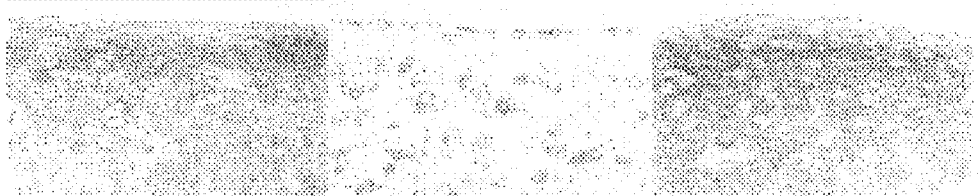
Figure 5A:
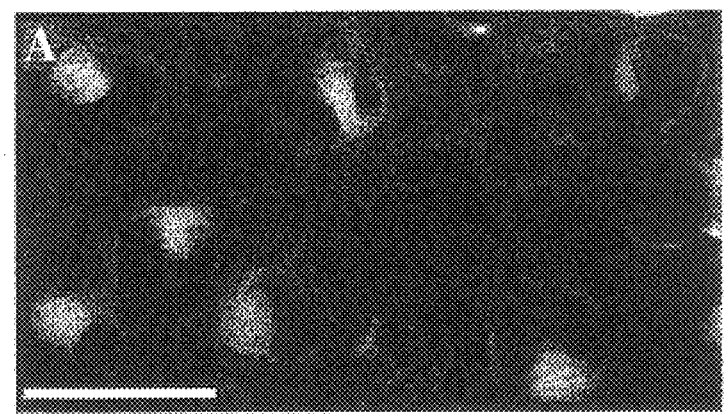
FIG. 5 (Panels A–C). F-actin stain of chondrocyte-polymer constructs. Constructs based on primary chondrocytes (A), and chondrocytes expanded for two passages without FGF-2 (B) and with FGF-2 (C), cultured for 1 week. Primary and FGF-2 expanded cells had a spherical morphology typical of differentiated chondrocytes, while cells expanded without FGF-2 had an elongated, fibroblast-like appearance, with abundant F-actin structures in the cytoplasm. Arrow indicates a residual polymer fiber. Scale bar=20 μm.
Figure 5B:
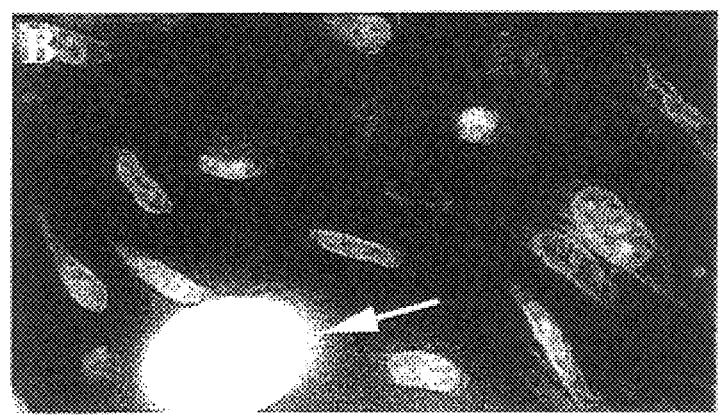
Figure 5C:
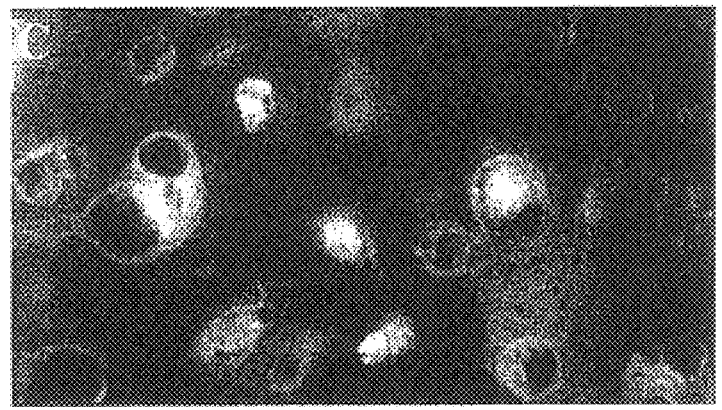

Chondrocytes expanded without FGF-2 displayed long, thick F-actin fibers, which were particularly evident after the second passage (FIG. 3A), while chondrocytes expanded in the presence of FGF-2 exhibited diffuse labeling for F-actin (FIG. 3B). In addition, chondrocytes that were expanded with FGF-2 during only the first passage and not the second passage developed thick F-actin fibers (FIG. 3C), while chondrocytes expanded without FGF-2 during the first passage and then with FGF-2 during the second passage showed a diffuse cytoplasmic staining for F-actin (FIG. 3D). Large, spread cellular morphology appeared to correlate with the presence of thick F-actin fibers (FIG. 3).

Example 2
Expansion of Human Chondrocytes

Human chondrocytes were isolated from hip and ankle articular surfaces of 25 to 66 year old patients undergoing join replacement following femoral neck fracture or soft tissue tumor resection. Cells were expanded in monolayers for 16 days (2 passages, approximately 5–9 doublings) in DMEM containing 10% FBS, and supplemented with FGF-2, transforming growth factor-β1 (TGFβ, epidermal growth factor (EGF), platelet-derived growth factor-bb (PDGF), or a combination of TGFβ and FGF-2 (T+F). The doubling times of chondrocytes were derived as described above. After each passage, the expression of specific genes (collagen type I and II, aggrecan and versican) was investigated at transcriptional level using real-time, quantitative PCR assays based on TaqMan fluorescence. The degree of differentiation was assessed as the ratio of collagen type II to type II (CII/CI) or aggrecan to versican (AGG/VER) at the mRNA level. Primary and P2 chondrocytes, expanded with and without FGF-2, were seeded on PGA meshes, cultured and assessed as described above for bovine chondrocytes. Primary and P2 chondrocytes, expanded in the presence of the different factors tested, were also centrifuged in polypropylene conical tubes to form spherical pellets ($5 \times 10^5$ cells/pellet). Pellets were cultured for 2 weeks either in DMEM containing serum and insulin, or in a defined (serum-free) medium, consisting of DMEM containing insulin, TGFβ and dexamethasone. Pellets were assessed histologically, biochemically, and using quantitative PCR. Duplicate samples from three independent experiments were analyzed.

Of all the factors tested during the expansion phase in monolayers, FGF-2 was the one that most increased the proliferation rate of human chondrocytes, in particular if used in combination with TGFβ(doubling times for cells cultured in control, FGF-2 and TGFβ+FGF-2 supplemented media were 76.6±3.9, 47.4±2.0 and 38.2±2.9 hours, respectively). Cell proliferation rate was inversely related to the stage of differentiation. P2 chondrocytes expanded under control conditions had CII/CI and AGG/VER ratios averaging 2% of those measured in primary chondrocytes before expansion, and these ratios were further reduced to 0.3% and 0.002% if cells were expanded in the presence of FGF-2 or TGFβ+FGF-2, respectively. The redifferentiation of expanded chondrocytes in pellet cultures showed that, irrespective of the conditions of cell expansion, CII/CI ratios were approximately 4 fold higher if pellets were cultured in defined medium, as opposed to medium containing serum. The highest extent of differentiation was detected in pellets based on TGFβ+FGF-2(CTR). In TGFβ+FGF-2 pellets, CII/CI and AGG/VER ratios were respectively 50 and 3 fold higher than in CTR pellets, and both ratios were as high as 50% of those measured in pellets based on primary chondrocytes.

The results have demonstrated that chondrocytes expanded under the conditions inducing the highest proliferation rate and the most enhanced dedifferentiation were those displaying the best ability to re-enter the differentiation program when transferred into a 3D environment. In particular, the serially passaged bovine chondrocytes cultured on PGA meshes regenerated cartilaginous tissues at rates and to degrees comparable to those observed for primary chondrocytes only if expanded in the presence of FGF-2. In addition, serially passaged adult human chondrocytes cultured in defined medium as pellets expressed the highest levels of differentiation markers, approximately 50% of the levels measured for primary chondrocytes, if expanded in the presence of TGFβ and FGF-2.

TABLE 1

Doubling times and alkaline phosphatase (AP) activities of chondrocytes in monolayers.

| Group | Doubling time (hours) | AP activity (% of primary chondrocytes)a |
|---|---|---|
| P1 | | |
| −FGF-2 | 18.9 ± 1.0 | 45.0 ± 7.4 |
| +FGF-2 | 13.9 ± 0.6* | 26.7 ± 0.9* |
| P2 | | |
| −FGF-2 | 13.6 ± 2.2 | 9.7 ± 1.6 |
| +FGF-2 | 12.4 ± 1.2 | 7.8 ± 0.3 | aAP activity of primary chondrocytes averaged 17.2 ± 0.4 Units/million cells
*Statistically significant difference from the corresponding control group (−FGF-2)

We claim:

1. A method of generating tissue comprising the steps of:
   (i) providing differentiated cells in a cell culture medium comprising fibroblast growth factor 2 in an amount sufficient to de-differentiate the differentiated cells;
   (ii) de-differentiating the differentiated cells and expanding the de-differentiated cells;
   (iii) harvesting the expanded cells; and
   (iv) generating a tissue in vivo or ex vivo using the harvested cells, wherein the differentiated cells are chondrocyte cells.

2. A method of generating tissue comprising the steps of:
   (i) providing differentiated cells in a cell culture medium comprising fibroblast growth factor 2 in an amount sufficient to de-differentiate the differentiated cells;
   (ii) de-differentiating the differentiated cells and expanding the de-differentiated cells;
   (iii) harvesting the expanded cells; and
   (iv) generating a tissue in vivo or ex vivo using the harvested cells, wherein the differentiated cells are mammalian chondrocyte cells.

3. A method of generating tissue comprising the steps of:
   (i) providing differentiated cells in a cell culture medium comprising fibroblast growth factor 2 in an amount sufficient to de-differentiate the differentiated cells;
   (ii) de-differentiating the differentiated cells and expanding the de-differentiated cells;
   (iii) harvesting the expanded cells; and
   (iv) generating a tissue in vivo or ex vivo using the harvested cells, wherein the differentiated cells are human chondrocyte cells.

4. A method of generating tissue comprising the steps of:
   (i) providing differentiated cells in a cell culture medium comprising fibroblast growth factor 2 in an amount sufficient to de-differentiate the differentiated cells;
   (ii) de-differentiating the differentiated cells and expanding the de-differentiated cells;
   (iii) harvesting the expanded cells; and
   (iv) generating a tissue in vivo or ex vivo using the harvested cells, wherein the differentiated cells are bovine chondrocyte cells.

5. The method of claim 1, wherein the cell culture medium comprises fibroblast growth factor 2 in an amount sufficient to maintain or induce an ability of the cells to respond to differentiation stimuli.

6. The method of claim 1, wherein the cell culture medium comprises fibroblast growth factor 2 in an amount sufficient to decrease doubling time of the cells.

7. The method of claim 1, wherein the step of de-differentiating the chondrocyte cells and expanding the de-differentiated cells further comprises transfecting the cells with nucleic acids.

8. A method of generating cartilaginous tissue comprising the steps of:
   (i) providing chondrocyte cells in a cell culture medium comprising fibroblast growth factor 2 in an amount sufficient to de-differentiate the chondrocyte cells;
   (ii) de-differentiating the chondrocyte cells and expanding the de-differentiated cells;
   (iii) harvesting the expanded cells; and
   (iv) generating a cartilaginous tissue in vivo or ex vivo using the harvested cells.

9. The method of claim 8, wherein the step of providing chondrocyte cells comprises providing mammalian chondrocyte cells.

10. The method of claim 8, wherein the step of providing chondrocyte cells comprises providing human chondrocyte cells.

11. The method of claim 8, wherein the step of providing chondrocyte cells comprises providing bovine chondrocyte cells.

12. The method of claim 8, wherein the cell culture medium comprises fibroblast growth factor 2 in an amount sufficient to maintain or induce an ability of the cells to respond to differentiation stimuli.

13. The method of claim 8, wherein the cell culture medium comprises fibroblast growth factor 2 in an amount sufficient to decrease doubling time of the cells.

14. The method of claim 8, wherein the step of de-differentiating the chondrocyte cells and expanding the de-differentiated cells further comprises transfecting the cells with nucleic acids.

15. A method of generating cartilaginous tissue comprising the steps of:
   (i) providing chondrocyte cells in a monolayer in a cell culture medium comprising fibroblast growth factor 2 in an amount sufficient to de-differentiate the chondrocyte cells;
   (ii) de-differentiating the chondrocyte cells and expanding the de-differentiated cells;
   (iii) harvesting the expanded cells; and
   (iv) generating a tissue in vivo or ex vivo using the harvested cells.

16. The method of claim 15, wherein the chondrocyte cells comprise mammalian chondrocyte cells.

17. The method of claim 15 wherein the chondrocyte cells comprise human chondrocyte cells.

18. The method of claim 15, wherein the chondrocyte cells comprise bovine chondrocyte cells.

19. The method of claim 15, wherein the cell culture medium comprises fibroblast growth factor 2 in an amount sufficient to maintain or induce an ability of the cells to respond to differentiation stimuli.

20. The method of claim 15, wherein the cell culture medium comprises fibroblast growth factor 2 in an amount sufficient to decrease doubling time of the cells.

21. The method of claim 15, wherein the step of de-differentiating the chondrocyte cells and expanding the de-differentiated cells further comprises transfecting the cells with nucleic acids.

* * * * *